(12) United States Patent
Lary et al.

(10) Patent No.: US 7,951,345 B2
(45) Date of Patent: May 31, 2011

(54) USEFUL SPECIMEN TRANSPORT APPARATUS WITH INTEGRAL CAPABILITY TO ALLOW THREE DIMENSIONAL X-RAY IMAGES

(75) Inventors: Todd P. Lary, Miami, FL (US); Banning Gray Lary, Miami, FL (US)

(73) Assignee: Lary Research & Development, LLC, Miami, FL (US)

( * ) Notice: Subject to any disclaimer, the term of this patent is extended or adjusted under 35 U.S.C. 154(b) by 545 days.

(21) Appl. No.: 12/129,807

(22) Filed: May 30, 2008

(65) Prior Publication Data

US 2008/0299605 A1 Dec. 4, 2008

Related U.S. Application Data

(60) Provisional application No. 60/932,626, filed on Jun. 1, 2007.

(51) Int. Cl.
*B01L 9/00* (2006.01)
(52) U.S. Cl. ........ 422/561; 422/82.05; 422/99; 422/102; 422/547; 422/560; 422/939; 422/940; 422/941; 422/942; 422/943; 422/944; 422/945; 422/946; 422/947; 422/948; 378/163; 378/165; 378/208; 435/30; 435/40.5; 435/283.1; 435/307.1; 436/57; 436/63; 600/310; 600/407; 600/426; 600/429; 600/584; 73/863; D10/64; D24/158
(58) Field of Classification Search ............... 422/82.05, 422/99, 102, 547, 560, 561, 939, 940, 941, 422/942, 943, 944, 945, 946, 947, 948; 378/163, 378/165, 208; 435/30, 40.5, 283.1, 307.1; 436/57, 63; 600/310, 407, 426, 429, 562, 600/584; 73/863; D10/64; D24/158
See application file for complete search history.

(56) References Cited

U.S. PATENT DOCUMENTS

| 4,993,056 | A |   | 2/1991  | Lary              |          |
|-----------|---|---|---------|-------------------|----------|
| 5,002,735 | A | * | 3/1991  | Alberhasky et al. | 422/82.05|
| 5,020,088 | A | * | 5/1991  | Tobin             | 378/164  |
| 5,061,452 | A | * | 10/1991 | Yamamoto et al.   | 422/536  |
| 5,105,457 | A | * | 4/1992  | Glassman          | 378/163  |
| 5,156,150 | A |   | 10/1992 | Lary              |          |
| 5,260,985 | A | * | 11/1993 | Mosby             | 378/164  |

(Continued)

OTHER PUBLICATIONS

Rebner, Marry et al. Two-View Specimen Radiography in Surgical Biopsy of Nonpalpable Breast Masses, American Journal of Roentgenology, (1987), 149:2, 283-285.

(Continued)

*Primary Examiner* — Lyle A Alexander
*Assistant Examiner* — Dennis M White
(74) *Attorney, Agent, or Firm* — McHale & Slavin, P.A.

(57) ABSTRACT

The present invention provides new and useful features and mechanisms for the localization and transport of biopsy specimens. The invention having a specimen board, an absorbent material in operative engagement and in coplanar alignment with the specimen board, a compression sheet, radio opaque indicia located within the specimen board, and a flexible connection between the compression sheet and the specimen board, and an attachment device which provides for removable engagement of the specimen board and compression sheet. The apparatus further provides for a clear visualization window and operating instructions. The absorbent material is capable of adjustable movement between a first and second position, providing orthogonal positioning relative to the specimen board. As a result, the apparatus may be used to create three dimensional radiographic images allowing tissue analysis resulting in orthogonal views while maintaining original positional reference points.

5 Claims, 6 Drawing Sheets

U.S. PATENT DOCUMENTS

| | | | |
|---|---|---|---|
| 5,323,443 A * | 6/1994 | Lary | 378/165 |
| 5,383,234 A | 1/1995 | Russell | |
| 5,383,472 A | 1/1995 | Devlin et al. | |
| 5,427,742 A * | 6/1995 | Holland | 422/536 |
| 5,476,016 A * | 12/1995 | Fedorka-Cray et al. | 73/863 |
| 5,568,534 A * | 10/1996 | Watkins | 378/208 |
| 5,609,827 A * | 3/1997 | Russell et al. | 422/559 |
| 5,702,128 A * | 12/1997 | Maxim et al. | 283/81 |
| 6,207,111 B1 * | 3/2001 | Weinberg | 422/82.05 |
| 6,216,379 B1 * | 4/2001 | Tanaka | 40/777 |
| 6,225,107 B1 | 5/2001 | Nagle | |
| 6,258,327 B1 * | 7/2001 | Tatum | 422/547 |
| 6,409,970 B1 * | 6/2002 | Phifer | 422/536 |
| 6,597,500 B1 * | 7/2003 | Burke et al. | 359/397 |
| 6,861,250 B1 * | 3/2005 | Cole et al. | 435/283.1 |
| 6,890,729 B2 * | 5/2005 | Mielzynska et al. | 435/40.5 |
| 7,147,826 B2 * | 12/2006 | Haywood et al. | 422/547 |
| 7,172,558 B2 * | 2/2007 | Olson, Jr. | 600/562 |
| 7,407,629 B2 * | 8/2008 | Mathews | 422/536 |
| 7,547,542 B2 * | 6/2009 | Bjornsen | 435/307.1 |
| 2005/0112032 A1 * | 5/2005 | McCormick | 422/102 |
| 2005/0112034 A1 * | 5/2005 | McCormick | 422/102 |
| 2005/0112758 A1 * | 5/2005 | Archambault et al. | 435/307.1 |
| 2007/0092412 A1 * | 4/2007 | Haywood et al. | 422/102 |
| 2007/0116612 A1 * | 5/2007 | Williamson | 422/102 |
| 2007/0183938 A1 * | 8/2007 | Booker | 422/102 |
| 2007/0237684 A1 * | 10/2007 | Hansen et al. | 422/102 |
| 2010/0075410 A1 * | 3/2010 | Desai et al. | 435/299.1 |

OTHER PUBLICATIONS

"Grid View Breast Biopsy Transport & Imaging", 2 pages, viewed at http//www.beekley.com/products/breast_biopsy.asp, on Aug. 15, 2008.

"Beekley Breast Biopsy Products", 10 pages and viewed at http://www.beekley.com/products/mainfraamebb.asp on Aug. 29, 2008.

"Two View Specimen Container", 2 pages, viewed at http://www.2-view.org/, on Aug. 29, 2008.

* cited by examiner

USEFUL SPECIMEN TRANSPORT APPARATUS WITH INTEGRAL CAPABILITY TO ALLOW THREE DIMENSIONAL X-RAY IMAGES

CROSS REFERENCE TO RELATED APPLICATION

This Application claims priority under 35 U.S.C. §119(e) to U.S. Provisional Application 60/932,626, filed on Jun. 1, 2007, the contents of which are herein incorporated by reference.

FIELD OF THE INVENTION

The invention relates to a device and method of use for transporting and localizing lesions or abnormalities in tissues; more specifically, to a device and method of use to transport and localize biopsy tissue where the tissue is fixed in a particular location for further medical analysis, including x-ray and pathology procedures. The device provides for a three dimensional visualization of the tissue and any possible lesions contained therein.

BACKGROUND OF THE INVENTION

It is estimated that over 10% of the female population in the United States will be affected by breast cancer at some point in their life. Currently, breast cancer is one of the most common cancers among American women, second only to skin cancer. It is responsible for more female-related cancer deaths than any other cancer, except lung cancer. Although the incidence of breast cancer has been declining since a sharp rise in the 1980s, it is estimated that over 182,000 new cases of invasive breast cancer will be diagnosed in women in the United States, with the chance of death resulting from breast cancer at about 1 in 35. Additionally, nearly 68,000 cases of carcinoma in situ, a non-invasive, early form of cancer will be diagnosed. Despite the fact that an estimated 45,000 women may die from the disease in 2008, actual death rates have been decreasing, generally attributed to earlier detection through screening, increased education and better treatment options.

In general, there is no specific sign or symptom definitively diagnosing cancer. Many common symptoms associated with cancers, such as weight loss, fatigue and even the development of a lump in certain areas of the body can be attributed to other ailments or harmless conditions. These symptoms, however, should not be ignored and are often used by medical professionals to perform further testing. In addition, early forms of some cancers can be detected through continuous screening methods.

Early screening for detection of breast cancer can start in a person's 20s and includes regular self-palpations and complete breast examinations. Completed by a health care professional, breast examinations consist of visual inspection and palpation of the breast, arm pits and areas around the collarbone. If a suspicious lump is detected, or as part of routine screening strategy, mammography, ultrasonography or magnetic resonance imaging (MRI) may be used to provide enhanced screening and diagnostic tools. Mammography is basically a set of x-rays of the breast which helps the diagnosing physician determine the nature of any abnormalities, particularly small non-palpable lesions. In many cases, these types of tests can aid the physician in the determination of whether the abnormality is breast cancer. However, such techniques are not 100% accurate and can miss approximately 10-15% of the breast cancer cases. Definitive diagnosis of breast cancer is only accomplished through the surgical removal of the tissue, or biopsy, for further examination by a radiologist and/or pathologist.

Locating, diagnosing and removing cancerous breast tissue requires pre and post-operative considerations. If the suspicious tissue is large enough for visualization or palpation, removal is generally not difficult. Localization of small, non-palpable tissue may be more difficult and time consuming as the surgical team uses x-rays to locate the area of concern and wire markers to mark it. Using a thin hollow needle the surgical team locates the area thought to contain the suspicious tissue as identified by a radiograph. A thin wire is inserted through the hollow needle to indicate placement of tissue removal. A hook at the end of the wire can be used to prevent the wire from slipping. The hollow needle is removed and the wire is used as a guide to locate the suspicious tissue. If the placement is correct and confirmed by a second x-ray, the tissue is removed and analyzed post-operatively. Several views of the removed tissue are often taken. This aids in localization and provides for identification of certain features of the sample which may not be identified by taking a single plane of view. Even if various features are identified from the multiple views, the final orientation may not correspond with the previous views. Taking radiographic views orthogonal to the original plane of orientation of the specimen can detect features that are undetectable in the original views. Post-operative analysis helps determine if the tissue is cancerous and whether or not the surgeon removed all the cancerous tissue. Further surgical excision may be required if cancerous tissue remains.

DESCRIPTION OF THE PRIOR ART

The present invention relates to an apparatus, and method of use, to transport and localize biopsy tissue where the tissue is fixed in a particular location for further medical analysis. Isolated tissue is removed during a surgical procedure and post-operatively analyzed. Post operative analysis includes detection and identification of cancerous cells within the tissue as well as localization of cancerous tissues relative to normal tissue. As a result, it is extremely important that the correct pre-operative location and orientation remains intact during all post-operative procedures.

As described in the Lary U.S. Pat. Nos. 4,993,056 and 5,156,150 localization and transportation of surgically removed tissue can contribute to inaccuracies and inefficiencies in the analysis process. Determination of the exact location of the cancer-specific area of the removed tissue can be difficult as a result of movement of the tissue during transportation, x-ray procedures, and pathological analysis. It is imperative that the correct orientation of the tissue remains intact as the pathologist making the final analysis must communicate information back to the surgeon. Inaccuracies in the process make it difficult for the pathologist to interpret and communicate to the surgeons the location of the cancerous tissue relative to where the surgeon removed the tissue and whether or not the surgeon removed all the cancerous tissue. As a result, patients may be subject to superfluous removal of body tissue and additional surgeries to remove the cancerous tissue not removed in the first surgery.

To address these difficulties, the '056 and '150 patents disclose an apparatus to secure the specimen during the transportation and pathological analysis in relation to a precise location defined by radio-opaque coordinates superimposed on the x-ray and method of use thereof. Inclusion of a fixed orientation and radio-opaque coordinates for the excised specimen on the x-ray helped the pathologist in localization of cancerous tissue within the removed sample and special coordination with the patient. In addition, the patents include an absorbent material on which the specimen naturally adheres and prevents movement.

The patented apparatus and method of use have been successfully manufactured by the MacBrud Corporation, Miami, Fla. under the trademarked name SPECBOARD and sold to various hospital departments and clinics world-wide for over 15 years. The success of the device relies on the fact that it allows quadrant identification to re-explore for missed lesions, enables accurate identification and localization, and has a precise reference grid and marking system which facilitates greater communication and cooperation among several medical disciplines. However, the '056 and '150 patents do not allow for the repositioning of the specimen in a regulated manner, providing a three dimensional view for the surgeon, radiologist or pathologists. As a result, true orthogonal views can not be achieved without removing the tissue from the device. However, removal of the tissue results in losing spatial orientation between the image and the original positioning. The invention according to the current application adds to the successful use and commercialization of the '056 and '150 patent by providing a new and novel apparatus which improves the usability and expands the capabilities of the patents previously described.

Therefore, if a device could be provided which allowed for three-dimensional tissue analysis resulting in orthogonal views while maintaining all original positional reference points, a long felt need would be realized.

Russell, U.S. Pat. No. 5,383,234, discloses a radiographic system for transporting and radiographically examining a tissue specimen without the risk of exposing workers to potentially hazardous tissue fluids. The system includes a transparent, sealable, liquid impervious container for receiving the tissue specimen and a tray positioned within the container for supporting the specimen. The tray has a first locating grid printed on one side and a second locating grid, which generates a radiographic image when exposed to x-rays, supported on the opposite side of the tray in registration with the first grid. Accordingly, when a tissue specimen is positioned on the first grid and then exposed to x-rays, a radiographic image of the specimen superimposed on the image of the second locating grid is produced. Since both locating grids are in registration, any tissue abnormality within the specimen can be precisely located with respect to both grids. However, the printed grid can obscure possible lesions if the lesions are on the grid line. The system does not provide for the structure and ability to radiographically examine the tissue specimen in a second plane, nor does it provide for a method to maintain the spatial positioning of the specimen.

Devlin et al., U.S. Pat. No. 5,383,472, discloses a system which permits a tissue specimen to be handled, inked, imaged in radiology and transported to pathology. The tissue specimen is inked by a solution injected into a sealed, disposable bag using a syringe which is attached to the bag. The inked tissue is removed from bag and placed upon fluid-absorbent blotter inscribed with a radiographically opaque grid, inside of a transparent container. However, the printed grid lines obscure the image, resulting in the possible covering of the lesions. Hinged top and bottom panels of the container secure the tissue specimen in place. The tissue specimen is visible from outside of the container during transport, x-ray imaging, and subsequent pathologic evaluation. In addition, the image presented to the pathologist with the inked tissue specimen permits identification of locations of suspect lesions or abnormalities. The pathologist can easily view the enclosed, undisturbed sample and associated x-ray prior to dissection of the tissue which can be performed within the apparatus if desired. The system lacks the structure and ability to radiographically examine the tissue specimen in a second plane and fails to provide a method for maintaining spatial orientation of the tissue and body.

Nagle, U.S. Pat. No. 6,225,107, discloses a specimen holder and transport device which can maintain an excised tissue sample in an orientation sufficient to determine its position in a body. The device permits radiological and pathological evaluation of a precisely and accurately oriented tissue specimen. The device includes an outer box open at one end for receiving the specimen, and an inner box for containing and minimally compressing the specimen. The specimen is marked and maintained in its in vivo orientation from the time of removal and is evaluated for location and orientation of a tumor during radiological and/or pathological assessments. The device permits the tissue sample to be radiologically examined in three planes and includes a limited marking system applied to the device. The Nagle device cannot be reduced in height to form a relatively thin and compact device. Moreover, this device prohibits further analysis of the specimen by a pathologist without the loss of orientation when it is removed from the container.

SUMMARY OF THE INVENTION

In view of the limitations now present in the prior art, the present invention provides new and useful features and mechanisms for the localization and transport of biopsy specimens. The invention having a specimen board, an absorbent material in operative engagement and in coplanar alignment with the specimen board, a compression sheet, radio opaque indicia located within the specimen board, and a flexible connection between the compression sheet and the specimen board. The apparatus also includes an attachment device providing for removable engagement of the specimen board and compression sheet.

In a particular embodiment, the specimen apparatus comprises a specimen board and an absorbent material in coplanar alignment with the specimen board. The absorbent material has a first portion and a second portion, the second portion adjustable between a first position and a second position. Adjustment between the positions provides orthogonal positioning relative to the first portion and the specimen board. The apparatus further comprises a compression sheet, a flexible connection between the compression sheet and the specimen board, radio opaque indicia, and an attachment device which provides for removable engagement of the specimen board and compression sheet. In addition, the specimen apparatus includes a selectively deployable support system positioned on the back-side surface of the absorbent material.

In another embodiment, the specimen apparatus comprises a specimen board, an absorbent material, a compression sheet, a flexible connection between the compression sheet and the specimen board, and an attachment device for removable engagement of the specimen board and said compression sheet. The absorbent material is in a juxtaposed relationship with the specimen board and in slideable engagement with a linking element. The linking element is constructed and arranged such that translation of the linking element in a plane parallel to the specimen board results in pivoting of the absorbent material to a position transverse to the specimen board.

Current products do not allow for the repositioning of the specimen in a regulated and controlled manner, nor do they provide fine resolution radio-opaque indicia. The repositioning mechanism allows the user to precisely reposition the specimen in the radio-opaque indicia frame of view and maintain its known orientation so that a true orthogonal x-ray may be taken of the specimen bordered by the radio-opaque indicia. This provides a three-dimensional view for the surgeon, radiologist and pathologist to more precisely locate lesions and abnormalities in tissue, such as breast tissue. The fine resolution markers on the grid indices allow for a more precise determination of the location of any abnormality. The clear window located in the compression cover allows the user to actually see where the specimen is located in the radio-opaque indicia during its operation.

Additionally, this improved specimen localization and transport device integrates the operating instructions and provides schematic diagrams, such as the breast, which are located on the compression sheet. This allows surgeons to indicate the position of biopsy removal and other markings for identification of the patient sample.

In accordance with this invention, "operative engagement" is understood to mean, and refers to the functional aspect that portions of the absorbent material are not completely and fully attached to the specimen board. As a result of this arrangement, portions of the absorbent material which are not completely attached to the specimen board are capable of adjustment between one or more positions independently of the specimen board. In the previous prior art, the specimen board and the absorbent material were completely and fully attached to each other. In that type of configuration, movement of the specimen board necessarily moves the absorbent material at the same time and in the direction.

In accordance with this invention, "flexible" is understood to mean any mechanism which provides for pivoting or rotational movement, such as but not limited to a hinge, a flexible strip connecting two materials together so as to create a hinge, or selectively removable interlocking mechanisms capable of rotational or pivoting movement.

In accordance with this invention, "attachment devices" is understood to mean any device capable of attaching objects together, including, but not limited to, snaps, ties, buttons, slots, hook and loop fasteners, or VELCRO.

Accordingly, it is a primary objective of the instant invention to provide for the precision orientation of a biopsy specimen during radiology and pathology.

It is a further objective of the instant invention to encompass a pivoting device that will allow the re-positioning of the biopsy such that an orthogonal image may be created in radiology.

It is yet another objective of the instant invention is to provide a fine resolution marking system on the radio-opaque indicia for abnormality localization.

It is a still further objective of the invention to provide a clear viewing of the biopsy during the compression of the specimen for localization in radiology.

It is a further objective of the instant invention to provide for the operating instructions on the cover along with breast schematic to allow input by the surgeon.

It is a still further objective of the invention to provide an enhanced grid system whereby division of the grid nomenclature is further resolved by additional markings manufactured into the radio opaque indicia grid system.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
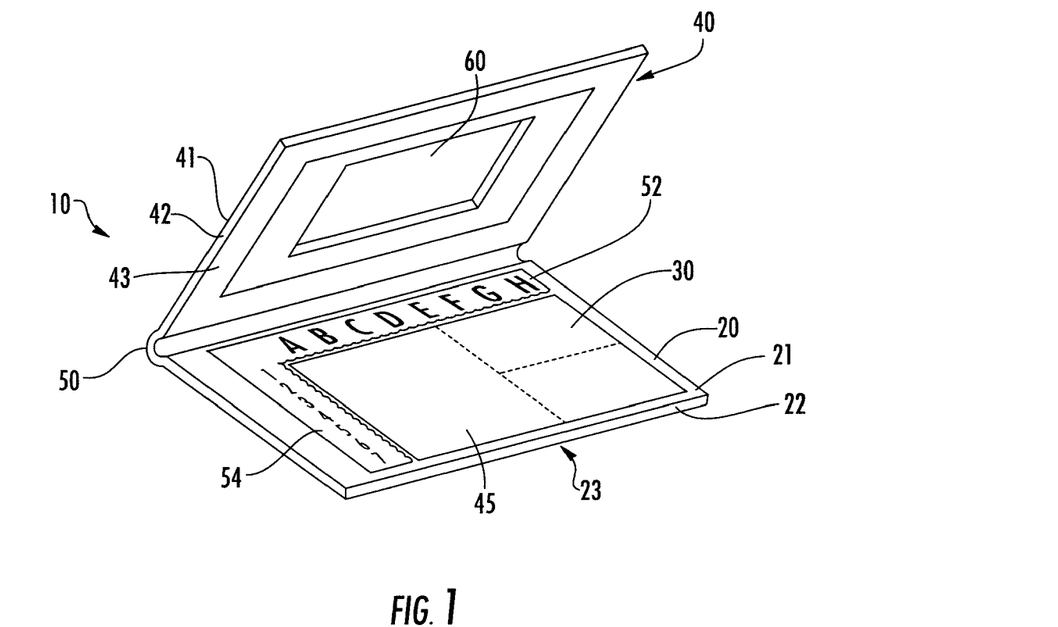
FIG. 1 is a perspective view of the specimen transport apparatus, indicating the compression sheet, specimen board, flexible absorbent material, radio-opaque indicia, and visualization window. As depicted, the apparatus is in an open position.

FIG. 1 is an illustration of the new and useful specimen transport apparatus with integral capability to allow three dimensional x-rays. The apparatus 10 contains a specimen board 20, an absorbent material 30, and a compression sheet 40. The specimen board 20 has a top surface 21, an inner surface 22 and a bottom surface 23. The compression sheet 40 contains a top surface 41, an inner surface 42 and a bottom surface 43. Specimen board 20 and compression sheet 40 are flexibly connected to each. The connection 50 allows the compression sheet 40 to fold directly on top of the specimen board 20 when apparatus 10 is in the closed position.

Figure 2A:
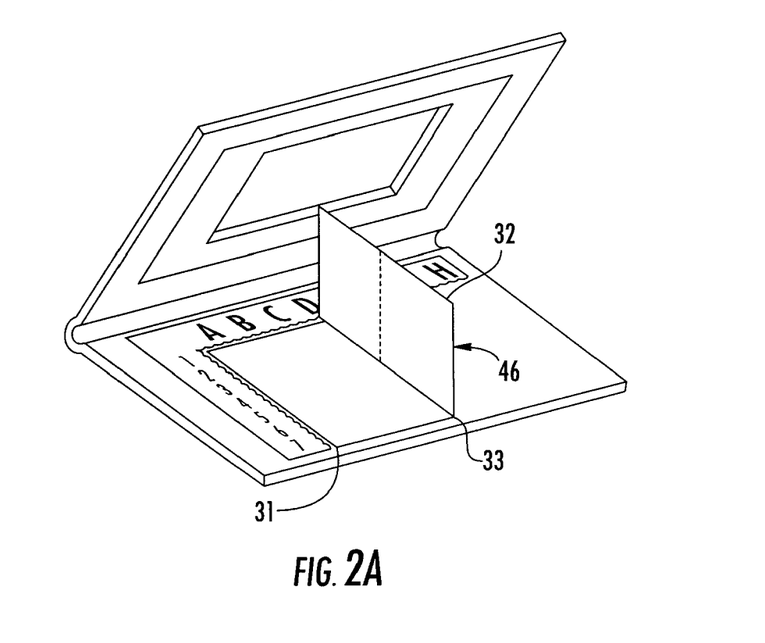
FIG. 2A illustrates the flexible absorbent material used to create true orthogonal radiographs allowing for the three-dimensional visualization of various body tissues and/or possible lesions. Such views can be used to determine the internal structure of the specimen located on and carried by the transporting apparatus without losing spatial orientation.

Attached to the specimen board 20 is a pivoting absorbent material 30. The absorbent material 30 is in operative engagement and in coplanar alignment with specimen board 20. The absorbent material has a front side surface 45 and a back-side surface, 46, see FIG. 2A. Absorbent material 30 can also be flexibly attached to the specimen board 20. As illustrated in FIG. 2A, the absorbent material 30 has two portions, a first portion 31 and a second portion 32. First and second portions 31 and 32, respectively, are interconnected along a folding line 33. Such arrangement allows first portion 31 to be attached to the specimen board 20. The flexible attachment provides the second portion 32 adjustable movement between a first position and a second position.

As illustrated in FIG. 2A, in a non-limiting embodiment, the second portion 32 has been lifted to a second position. In the first position, second portion 32 is parallel to the specimen board. As the second portion 32 is adjusted to a second position, it is moved upwardly 90 degrees relative to the horizontal plane of the specimen board 20. The flexible attachment and pivoting movement allows the apparatus to provide new and useful features and mechanisms for the localization and transport of the biopsy specimen. Such arrangement allows for the repositioning of the specimen in a controlled and regulated manner. Repositioning allows the user to maintain the exact position so that orthogonal x-rays may be taken of the specimen. This ability provides a three-dimensional view for the surgeon, radiologist and pathologist and helps locate any tissue abnormality by precisely determining its location.

Figure 2B:
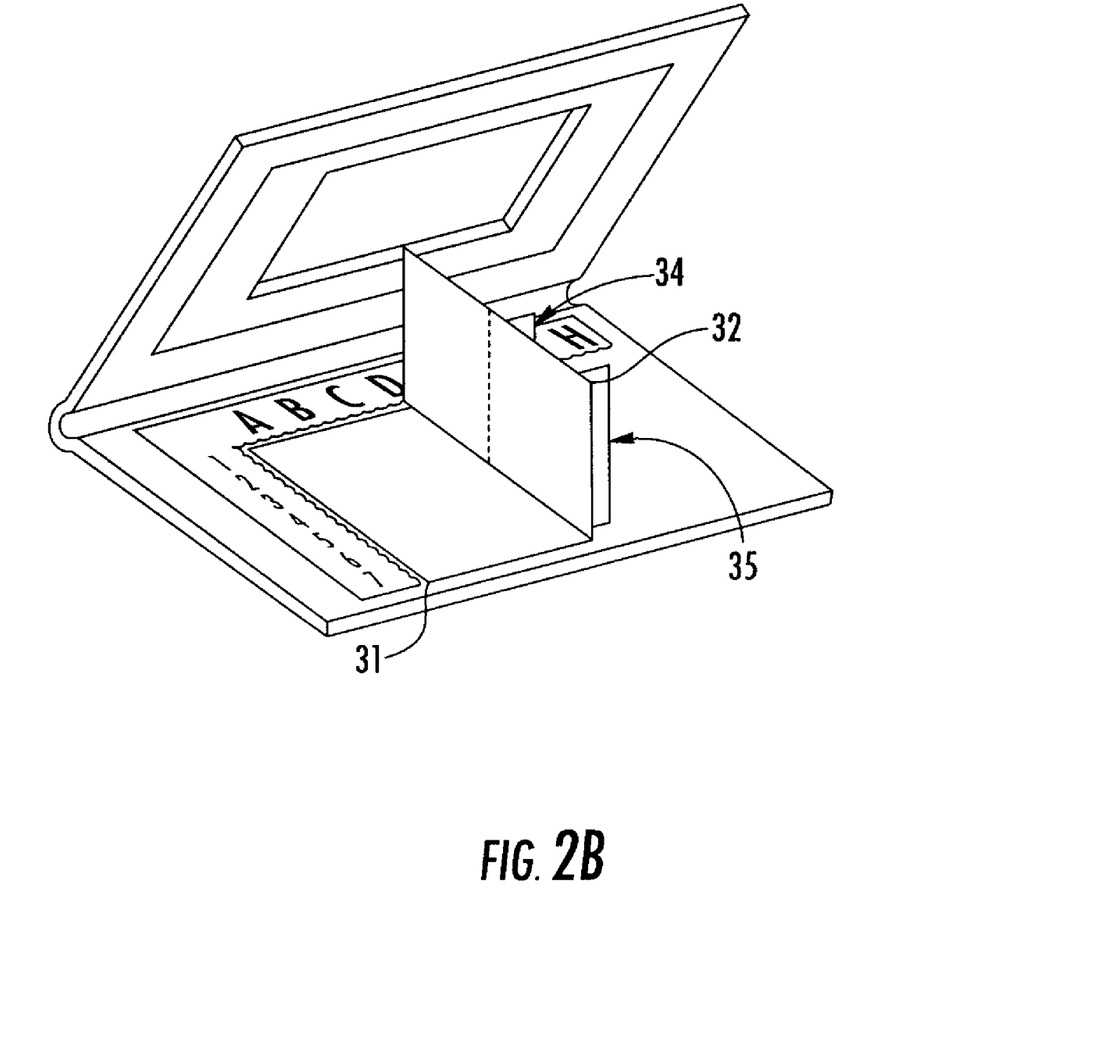
FIG. 2B demonstrates a particular embodiment of the apparatus, illustrating an absorbent material including two portions. As illustrated, the second portion is in the raised position and depicts the selectively deployable support system.

FIG. 2B illustrates a selectively deployable support system, 34 and 35, for a particular embodiment of the absorbent material. The support system attaches to the back-side surface 46 of the second portion 32 of absorbent material 30. The support system 34 and 35 is capable of folding to a compact position. Such a closed position allows the absorbent material to be positioned in an un-folded and generally flat position. Upon extending second portion 32 upwardly, support systems 34 and 35 can be extended outwardly and positioned to rest along portions of the surface of specimen board 20. It can be appreciated that any system that can be deployable and used to support the second panel can be used, including, but not limiting to, a single panel, a foot, an anchor, or even having the second panel being flexible such that a portion of the front-side surface of the panel can pivot towards its back-side surface.

Figure 2C:
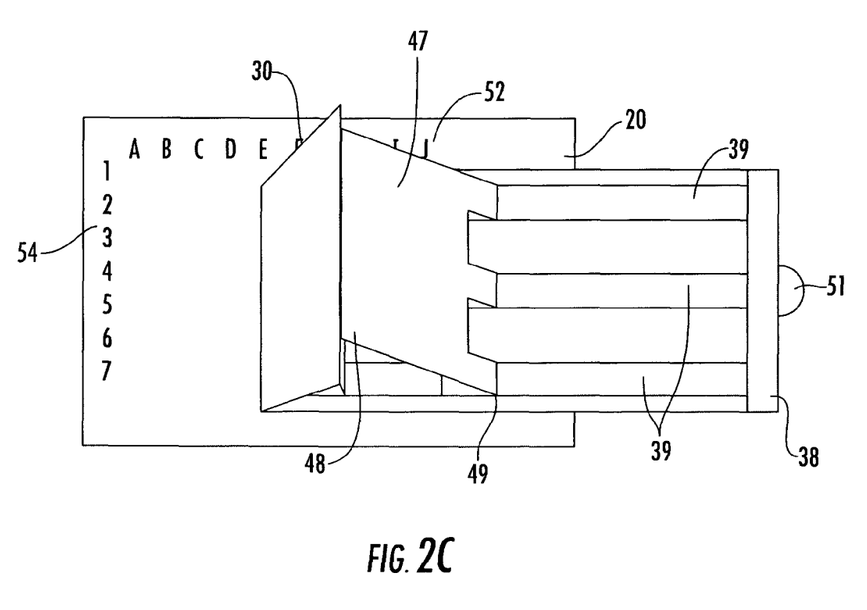
FIG. 2C demonstrates a further embodiment of the apparatus, illustrating the relationship between the absorbent material, linking element, and specimen board.

FIG. 2C illustrates another embodiment of the specimen apparatus 10. According to this embodiment, absorbent material 30 is in a juxtaposed relationship with the specimen board 20 and in slideable engagement with a linking element. The linking element is constructed and arranged such that translation of the linking element in a plane parallel to the specimen board results in pivoting of the absorbent material to a position transverse to the specimen board. The linking element is further defined by a slideable structure 38 and a support structure 47. The absorbent material 30 can be pivotally coupled to the slideable structure 38 by a common hinge line 37 that extends the length of the absorbent material and slideable structure. The slideable structure 38 can be further defined by alternating openings 39. Support structure 47 has a first end 48 affixed to the back-side surface of the absorbent material 30. The second end 49 is affixed to the front-side surface of the specimen board 20. The second end 49 further has one or more portions constructed and arranged to engage the slideable structure in a manner that allows passage of one or more portions of the slideable structure through the support structure and/or provides one or more portions of the support element movement within the slideable element.

Figure 3A:
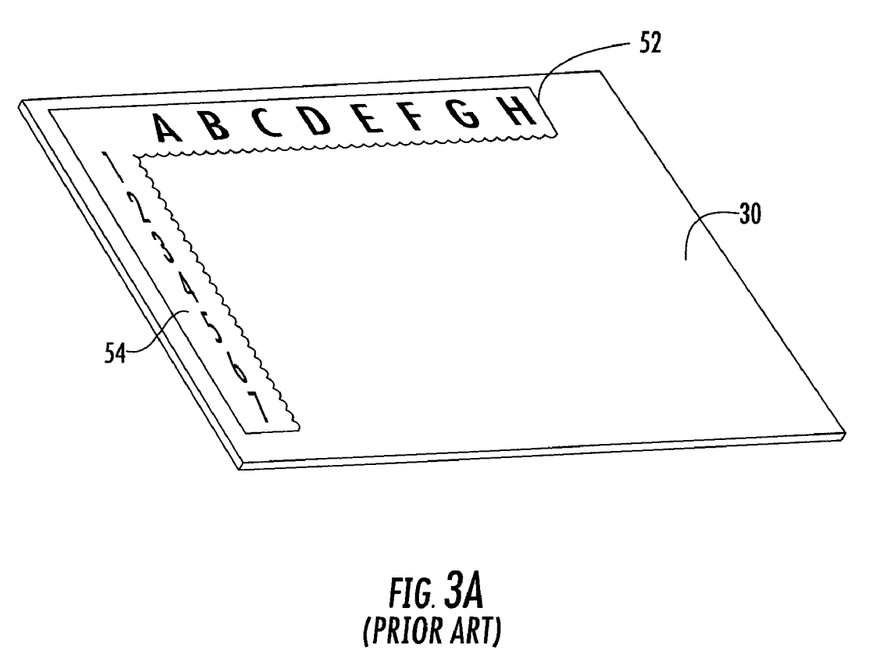
FIG. 3A is a detailed view of the radio-opaque indicia.
Figure 3B:
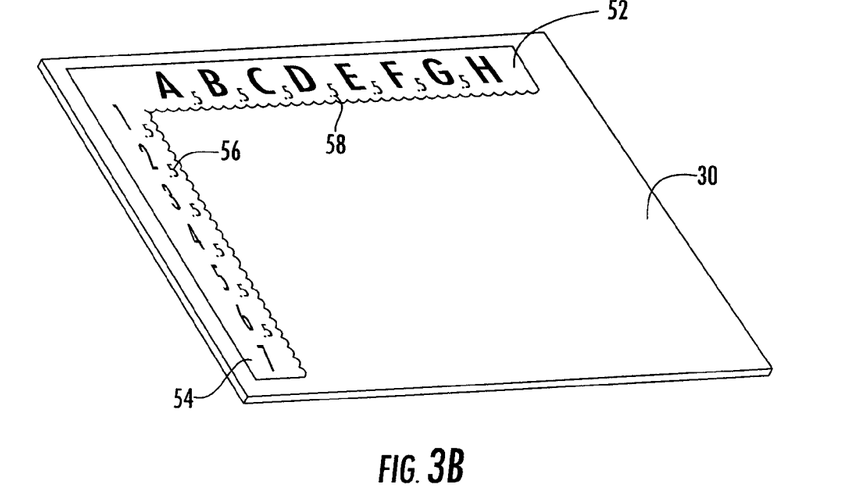
FIG. 3B is an embodiment of an enhanced grid system.

As illustrated in FIG. 3A, the specimen board 20 contains strips of radio opaque material 52 and 54 located on the specimen board bordering the absorbent material 30. In this view, radio opaque strip 52 contains a series of radio-opaque letters. Radio opaque strip 54 contains a series of radio-opaque numbers. It can be appreciated that any type of identification marker or symbol can be used in either strip 52 or 54. In addition to the numbers or letters represented on the radio opaque indicia one or more subdivisions may be positioned between each number and letter respectively to create an enhanced grid system which provides more specific coordinates for communicating specimen position. FIG. 3B represents an embodiment of an enhanced grid system, using subdivision markings, 56 and 58, placed in between the letters 52 and numbers 54 on the radio opaque strips to represent additional reference points. In addition to numbers as illustrated by FIG. 3B, a grid system providing higher resolution capabilities using finer references such that divisions of the grid nomenclature, such as "123" and "ABC", are further resolved by a number of additional subdivisions or markings, such as but not limited to numbers, letters or symbols, lines, physical notches, or points, manufactured into or placed onto the radio opaque strips between each letter and/or number, respectively, is provided. Such additional subdivisions allow the user to more clearly identify and communicate lesion positions. In the previous system, if the user identified a lesion corresponding to the areas associated with A and B and between 3 and 4, a user could only communicated the position as between A and B and 3 and 4. With the enhanced grid system, additional subdivisions within the radio opaque indicia allow a user better communication by reporting the lesion location at, for example, A.5 and 3.

Figure 4:
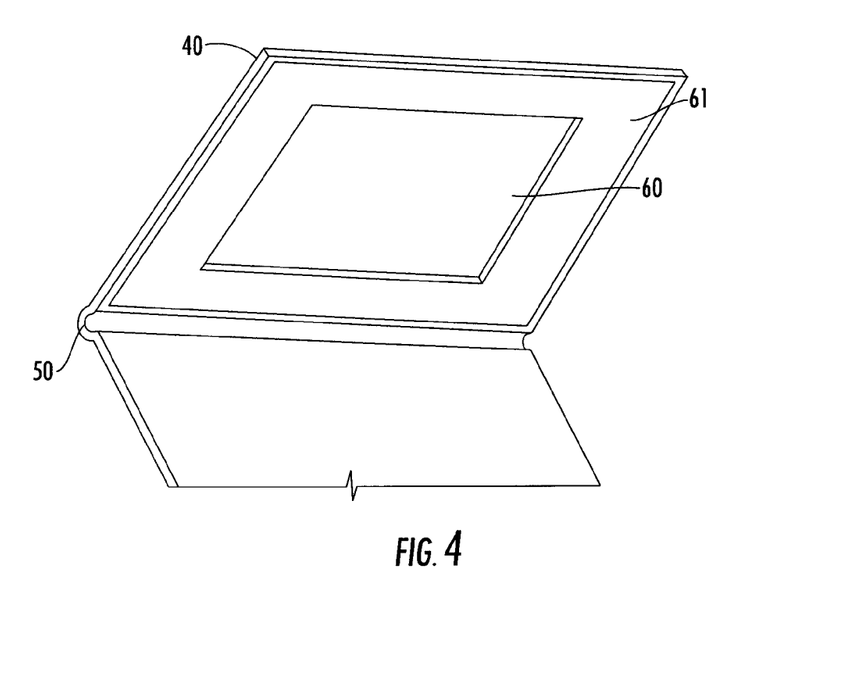
FIG. 4 is a detailed view of the visualization window.

Within compression sheet 40 is visualization window 60, see FIG. 4. Visualization window 60 can be constructed of any materials and to any shape or size which allows for visualization of contents placed within the apparatus. The clear visualization window provides the user with the ability to visualize specimen location. In addition, the compression sheet also contains a release coating 61, such as TEFLON or a silicon material that prevents the tissue sample from adhering to the compression sheet.

Figure 5:
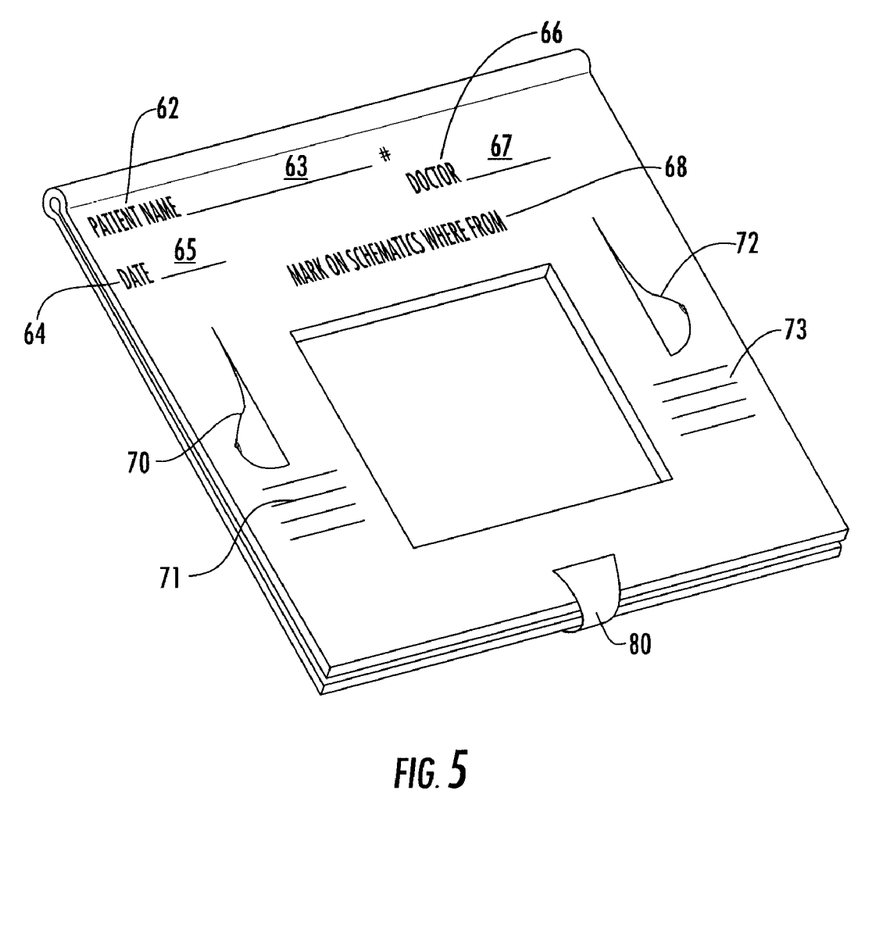
FIG. 5 is a detailed view of the front cover of the apparatus, illustrating the integrated operating instructions and schematic diagrams of the compression sheet.

FIG. 5 is a diagrammatic representation of the top portion of the compression sheet 40. The top portion of the compression sheet is the front cover of apparatus 10 when the apparatus is in the closed position. Integrated within the compression sheet 40 are operating instructions and diagrammatic schematics. As illustrated in FIG. 5, operating instructions can include, but not limited to, patients name, 62, date, 64, identification of physician/surgeon, 66, and blank spaces 63, 65, and 67, respectively, to fill in such information. Furthermore, various user instructions may be placed on the sheet as well, 68. In addition to operating instructions, diagrammatic schematics can be placed on the compression sheet. As further illustrated in FIG. 5, schematic diagrams of the right 70 and left 72 human breasts with blank spaces, 71 and 73, for additional comments are included. It can be appreciated that although the diagram includes illustrations of the human breast, any schematic may be included. FIG. 5 also includes a closure apparatus 80 which is used to attach specimen board 20 to compression sheet 40. Such closure apparatus can include any manner that maintains the compression sheet and specimen board in a closed position, including but not limited to snaps, buttons, and hooks and loop fasteners.

The new and improved specimen transport apparatus can be used during the tissue biopsy process to transport and help localize lesions within tissue samples. The description, as described below, includes removal and analysis of breast tissue, however, it can be appreciated that removal of any tissue can be utilized in the inventive method. At the surgery site, the surgeon receives apparatus 10 containing a specimen board 20, an absorbent material 30, and compression sheet 40. The surgeon removes the breast tissue according to standard operating procedures and tissue removal protocols. The surgeon, or member of the surgical team, can mark on the operating instructions (62,63,64,65,66,67,68) and schematic diagrams (70,71,72,73) integrated within apparatus 10 important and relevant information, including location and/or orientation in the body where the tissue was removed. The removed tissue is placed on the absorbent material 30 and adheres to the absorbent material 30. The compression sheet 40 which is connected to specimen board 20 by a flexible connection 50 is folded over the absorbent material 30. The apparatus is sealed using an attachment device 80 for removable engagement of the specimen board and the compression sheet. The apparatus is then transported from the surgical site to be analyzed by radiologists using radiographic analysis. With this apparatus, radiologists, or technicians, can take additional views of the tissue by pivoting or moving the absorbent material. Possible tissue abnormalities are noted by radiology according to location as related to the radio-opaque indicia 52, 54.

In a particular embodiment, the surgeon places excised tissue onto an absorbent material as illustrated in FIG. 2B.

After excising the sample, the surgeon specifically places the sample on the second portion 32 of absorbent material 30 before placing the compression sheet 40 over the specimen and closing the apparatus. Samples are transported to radiology and x-rays are taken. To achieve additional views, the radiologist, or technician, removes the compression sheet 40. The second portion 32 of the absorbent material 30 is lifted to a second position by extending the second portion 90 degrees in an upward motion relative to the specimen board 20. Second portion 32 is held in place by extending the selectively deployable support system 34, 35, which during transportation and initial x-ray were in a folded, compact position. The extended support system 34, 35 is supported by the surface of the specimen board 20. This allows reorientation of the tissue, allowing radiology to take true orthogonal views while maintaining the proper spatial orientation.

According to a different embodiment, the surgeon places excised tissue onto an absorbent material as illustrated in FIG. 2C. The tissue may be placed along any portion associated with the absorbent material 30, but preferably at the left edge near radio-opaque indicia 54. The specimen is secured within the apparatus by placing the compression sheet on top of the specimen board and sealing the device closed. Samples mat be transported to radiology and x-rays taken. In some situations, radiology may be performed in the operating room where the apparatus may be placed on a small x-ray machine located in the room. The apparatus may be manipulated such that translation of the linking element in a plane parallel to the specimen board results in pivoting of the absorbent material to a position transverse to the specimen board. To accomplish this, the radiologist, or technician, removes the compression sheet 40 and causes the absorbent material 30 to move to a second position, preferably 90 degrees relative to the specimen board 20 by using a device for selectively moving the slideable structure along a horizontal plane such as, but not limited to a pull tab 51 (FIG. 2C). As the user pulls on the tab, portions of the support structure 47 move through portions of the slideable structure and within the openings 39 of the slideable structure.

In this configuration the tissue can be reoriented while maintaining all original positional reference points, allowing radiology to create true orthogonal images without losing orientation. After the complete set of x-rays is taken, the absorbent material may be placed in the flat, compact position by pushing on the tab. Noting the corresponding coordinates as indicated from the radio-opaque indicia, additional procedures, such as pathological analysis, maybe undertaken. This method allows the pathologist to locate the specific location of the suspect area of the tissue. An additional advantage of the apparatus used in the method is that pathological analysis can be performed within the apparatus. Results of the analysis are interpreted and reported to the surgical team or to the patient post-operatively.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A specimen apparatus comprising a specimen board, an absorbent material, said absorbent material in a juxtaposed relationship with said specimen board and in slidable engagement with a linking element, said linking element constructed and arranged such that translation of said linking element in a place parallel to said specimen board results in pivoting of said absorbent material to a position transverse to said specimen board, a compression sheet, a flexible connection between said compression sheet and said specimen board, said specimen board including radio opaque indicia, and an attachment device for removable engagement of said specimen board and said compression sheet.

2. A specimen apparatus according to claim 1 further comprising an enhanced grid system.

3. The specimen apparatus according to claim 2 wherein said compression sheet further includes a visualization window.

4. The specimen apparatus according to claim 3 wherein said compression sheet further includes operating instructions and schematic diagrams.

5. The specimen apparatus according to claim 4 wherein said schematic diagrams are of the breast.

* * * * *